(12) United States Patent
Nakayama

(10) Patent No.: US 10,254,302 B2
(45) Date of Patent: Apr. 9, 2019

(54) METHOD FOR CLINICAL EXAMINATIONS AND CLEANING METHOD THEREFOR

(71) Applicant: JEOL Ltd., Tokyo (JP)

(72) Inventor: Yoshiyuki Nakayama, Tokyo (JP)

(73) Assignee: JEOL Ltd., Tokyo (JP)

( * ) Notice: Subject to any disclaimer, the term of this patent is extended or adjusted under 35 U.S.C. 154(b) by 78 days.

(21) Appl. No.: 15/297,827

(22) Filed: Oct. 19, 2016

(65) Prior Publication Data

US 2017/0131313 A1 May 11, 2017

Related U.S. Application Data

(62) Division of application No. 13/495,116, filed on Jun. 13, 2012, now abandoned.

(30) Foreign Application Priority Data

Jun. 14, 2011 (JP) .................. 2011-131968
Apr. 25, 2012 (JP) .................. 2012-099644
May 22, 2012 (JP) .................. 2012-116107

(51) Int. Cl.
*G01N 35/10* (2006.01)
*B08B 3/08* (2006.01)
*G01N 35/04* (2006.01)

(52) U.S. Cl.
CPC ........... *G01N 35/1004* (2013.01); *B08B 3/08* (2013.01); *G01N 2035/0437* (2013.01)

(58) Field of Classification Search
CPC .................. G01N 35/1004; G01N 2035/0437
See application file for complete search history.

(56) References Cited

U.S. PATENT DOCUMENTS

| 5,948,358 A * | 9/1999 | Saito ...................... B01L 99/00 |
| | | 134/169 R |
| 2010/0108097 A1* | 5/2010 | Xueping .................. B08B 9/00 |
| | | 134/18 |

FOREIGN PATENT DOCUMENTS

| JP | 8101214 A | 4/1996 |
| JP | 200968879 A | 4/2009 |

* cited by examiner

*Primary Examiner* — Kathryn Wright
(74) *Attorney, Agent, or Firm* — The Webb Law Firm

(57) ABSTRACT

An method is offered which can clean the nozzles of a reaction cuvette wash unit. A first detergent is put in first reagent containers located on a first reagent turntable. A computer controller drives a first reagent pipette to aspirate the detergent from the first reagent containers and to deliver the detergent into reaction cuvettes. The controller drives a reaction turntable to bring each reaction cuvette holding the detergent therein to the reaction cuvette wash unit. The controller drives the reaction cuvette wash unit to aspirate the detergent from inside the reaction cuvettes using reaction cuvette wash nozzles to thereby clean the wash nozzles. A second detergent is then used to clean the nozzles.

1 Claim, 5 Drawing Sheets

METHOD FOR CLINICAL EXAMINATIONS AND CLEANING METHOD THEREFOR

CROSS REFERENCE

This application is a divisional application of U.S. patent application Ser. No. 13/495,116 filed Jun. 13, 2012, which is hereby incorporated by reference in its entirety.

BACKGROUND OF THE INVENTION

Field of the Invention

The present invention relates to an automated analyzer for clinical examinations and, more particularly, to an automated clinical analyzer having a sample turntable on which sample containers are set, a reagent turntable on which reagent containers are set, a reaction turntable on which reaction cuvettes are set, a reagent pipette for aspirating a reagent from each of the reagent containers on the reagent turntable and delivering the reagent into the reaction cuvettes on the reaction turntable, a reaction cuvette wash unit for delivering and aspirating a detergent into and from the reaction cuvettes set on the reaction turntable via reaction cuvette wash nozzles to clean the inside of each reaction cuvette, and control device for controlling the operation of the sample turntable, reagent turntable, reaction turntable, reagent pipette, and reaction cuvette wash unit.

Description of Related Art

In an automated clinical analyzer as shown in JP-A-8-101214 and JP-A-2009-68879 given below, a reaction cuvette wash unit is mounted to clean reaction cuvettes set on a reaction turntable.

FIG. 5 shows one example of the reaction cuvette wash unit. The shown wash unit, indicated by reference numeral 23, is installed at a given wash position on a reaction turntable 12 on which a multiplicity of reaction cuvettes 11 are arrayed. The reaction cuvette wash unit 23 has a plurality of exhaust nozzles S1-S5, a plurality of injection nozzles I1-I4, and a drying nozzle SD for drying the insides of the reaction cuvettes. Each pair or each one of the nozzles is held separately by holders H1-H6, which are spaced apart by a distance corresponding to two of the reaction cuvettes. The holders are held integrally by a frame F. The nozzles are simultaneously inserted into the reaction cuvettes by making the frame F descend and are simultaneously drawn from the reaction cuvettes by making the frame F ascend after the end of a wash operation. An anti-overflow nozzle (not shown) is combined with each injection nozzle to prevent overflow by sucking the liquid when the liquid level reaches a given height.

The reaction turntable 12 makes an angular movement through a given angle in the direction indicated by the arrows and stops. The turntable 12 moves and stops in this way repeatedly. When some reaction cuvette A comes to a stop in position A(1), the cuvette then comes to a stop at position A(2) ahead of the reaction cuvette wash unit 23. Then, the cuvette stops at positions A(3), A(4), A(5), and A(6) in turn.

When the reaction cuvette A is at halt at the position A(1), the exhaust nozzle S1 held to the holder H1 aspirates reaction liquid undergone a measurement and vents the liquid into the waste tank. The injection nozzle I1 injects a rinse fluid or rinse water into the reaction cuvette from which the reaction liquid has been discharged.

At the next timing point of halt, the reaction cuvette A is halted in the position A(2). The exhaust nozzle S2 held to the holder 112 aspirates the rinse fluid from this cuvette A and discharges it into the waste tank. The injection nozzle I2 injects a detergent.

At the next timing point of halt, the reaction cuvette A is halted in the position A(3). The exhaust nozzle S3 held to the holder 113 draws in the detergent from the cuvette A and vents it into the waste tank. The injection nozzle I3 injects a rinse fluid or rinse water into the reaction cuvette from which the detergent has been discharged.

At the next timing point of halt, the reaction cuvette A is halted in the position A(4). The exhaust nozzle S4 held to the holder H4 aspirates rinse fluid from this cuvette A and discharges the fluid into the waste tank. The injection nozzle I4 again injects a rinse fluid or rinse water into the reaction cuvette from which the rinse fluid has been discharged.

At the next timing point of halt, the reaction cuvette A is halted in the position A(5). The exhaust nozzle S5 held to the holder H5 draws in the rinse fluid and discharges it into the waste tank.

At the next timing point of halt, the reaction cuvette A is halted in the position A(6). The drying nozzle SD held to the holder H6 completely aspirates the rinse fluid remaining on the bottom and inner wall of the cuvette and discharges the fluid, thus drying the cuvette.

After the reaction cuvette has been cleaned by the use of the reaction cuvette wash unit 23 as described above, the reaction cuvette is used for anew sample analysis.

The reaction cuvette wash unit 23 is used for analysis routine cleaning as described above during a process for analysis. In addition, the wash unit 23 is also employed in a daily cleaning mode in which each reaction cuvette is cleaned once or twice per day. In this daily cleaning mode, the reaction turntable and reaction cuvette wash unit 23 are run in the same way as in normal analysis. However, no sample is supplied into the reaction cuvettes. A detergent for daily cleaning is supplied successively into all reaction cuvettes on the reaction turntable via a reagent pipette. Because of this daily cleaning using the reaction cuvette wash unit 23, residues adhering to the inner wall of each reaction cuvette that cannot be sufficiently removed by the analysis routine cleaning can be washed away.

It is considered that the nozzles of the reaction cuvette wash unit 23 are also cleaned by suction of the detergent during the processes of analysis routine cleaning and daily cleaning but it has been difficult to completely prevent adhesion of residuals to all the nozzles of the reaction cuvette wash unit. Therefore, when the automated analyzer for clinical examinations is run for a long time, the phenomenon that some of the nozzles of the reaction cuvette wash unit become clogged is produced.

Where such nozzles were clogged in the past in this way, the human operator removed the nozzles together with the frame F, filled cuvettes (e.g., sample tubes) adapted for the nozzle shape with a detergent, aspirated the detergent via the nozzles to thereby clean them, and then attached the nozzles.

In JP-A-8-101214, there is no mention of wash of a reaction cuvette wash unit. However, regarding wash of the nozzle of a pipette, there is the aforementioned mention of a method of wash. In JP-A-2009-68879, there is no mention of wash of a reaction cuvette wash unit in the same way as JP-A-8-101214 but a mechanism of wash the nozzle of a pipette using sonic waves is set forth.

However, if any of the methods of wash nozzles of pipettes as set forth in JP-A-8-101214 and JP-A-2009-68879 are used for a reaction cuvette wash unit, a separate mechanism is necessary, thus presenting a problem.

SUMMARY OF THE INVENTION

In view of the foregoing problem, the present invention has been made. It is an object of the present invention to provide an instrument and method which is used for clinical examinations and which can wash the nozzles of a reaction cuvette wash unit with simple manipulations by having a nozzle cleaning mode although the instrument has a simple structure. It is another object to provide a cleaning method adapted to be implemented by this instrument.

A first embodiment of the present invention provides an automated clinical analyzer having: a sample turntable on which sample containers are set; a reagent turntable on which reagent containers are set; a reaction turntable on which reaction cuvettes are set; a sample pipette for delivering a sample into the reaction cuvettes on the reaction turntable; a reagent pipette for aspirating a reagent from each of the reagent containers on the reagent turntable and delivering the aspirated reagent into the reaction cuvettes on the reaction turntable; a reaction cuvette wash unit for cleaning the reaction cuvettes set on the reaction turntable, the reaction cuvette wash unit having plural wash nozzles for aspirating reaction liquids from inside the reaction cuvettes, delivering and aspirating a first detergent, and delivering and aspirating a rinse fluid; and control device for controlling the operation of the sample turntable, reagent turntable, reaction turntable, reagent pipette, and reaction cuvette wash unit. A second detergent is placed in a position where the second detergent can be drawn in by the reagent pipette. The control device drives the reagent pipette to aspirate the second detergent and to deliver it into the reaction cuvettes. The control device drives the reaction turntable to move each of the reaction cuvettes holding the second detergent therein to the position of a preset one of the wash nozzles of the reaction cuvette wash unit and to cause this wash nozzle to descend for aspirating the second detergent from inside the reaction cuvette.

An eighth embodiment of the invention provides a cleaning method adapted to be implemented in an automated analyzer for clinical examinations having a sample turntable on which sample containers are set, a reagent turntable on which reagent containers are set, a reaction turntable on which reaction cuvettes are set, a reagent pipette for aspirating a reagent from each of the reagent containers on the reagent turntable and delivering the aspirated reagent into the reaction cuvettes on the reaction turntable, a reaction cuvette wash unit for cleaning the reaction cuvettes set on the reaction turntable, the reaction cuvette wash unit having plural wash nozzles for aspirating reaction liquids from inside the reaction cuvettes, delivering and aspirating a first detergent, and delivering and aspirating a rinse fluid, and control device for controlling the operation of the sample turntable, reagent turntable, reaction turntable, reagent pipette, and reaction cuvette wash unit. The wash method starts with placing a second detergent in a position where the second detergent can be aspirated by the reagent pipette. Then, the reagent pipette is driven such that the second detergent is aspirated and delivered into the reaction cuvette (hereinafter may be referred to as the first step). Then, the reaction turntable is driven to move the reaction cuvette holding the second detergent into the position of a specified one of the wash nozzles of the reaction cuvette wash unit (hereinafter may be referred to as the second step). The wash nozzle is made to descend to aspirate the second detergent from inside the reaction cuvette (hereinafter may be referred to as the third step).

According to the aforementioned first or eighth embodiment of the invention, the reagent pipette is driven to aspirate the second detergent and to deliver it into the reaction cuvette. The reaction turntable is driven to move the reaction cuvette containing the second detergent into the specified cleaning nozzle of the reaction cuvette wash unit. The second detergent is aspirated from inside the reaction cuvette using this wash nozzle, thus cleaning the wash nozzle. Consequently, each wash nozzle of the reaction cuvette wash unit can be cleaned with simple structure and simple manipulations.

DESCRIPTION OF THE PREFERRED EMBODIMENTS

An automated clinical analyzer according to one embodiment of the present invention is described with reference to the drawings.

Figure 1:
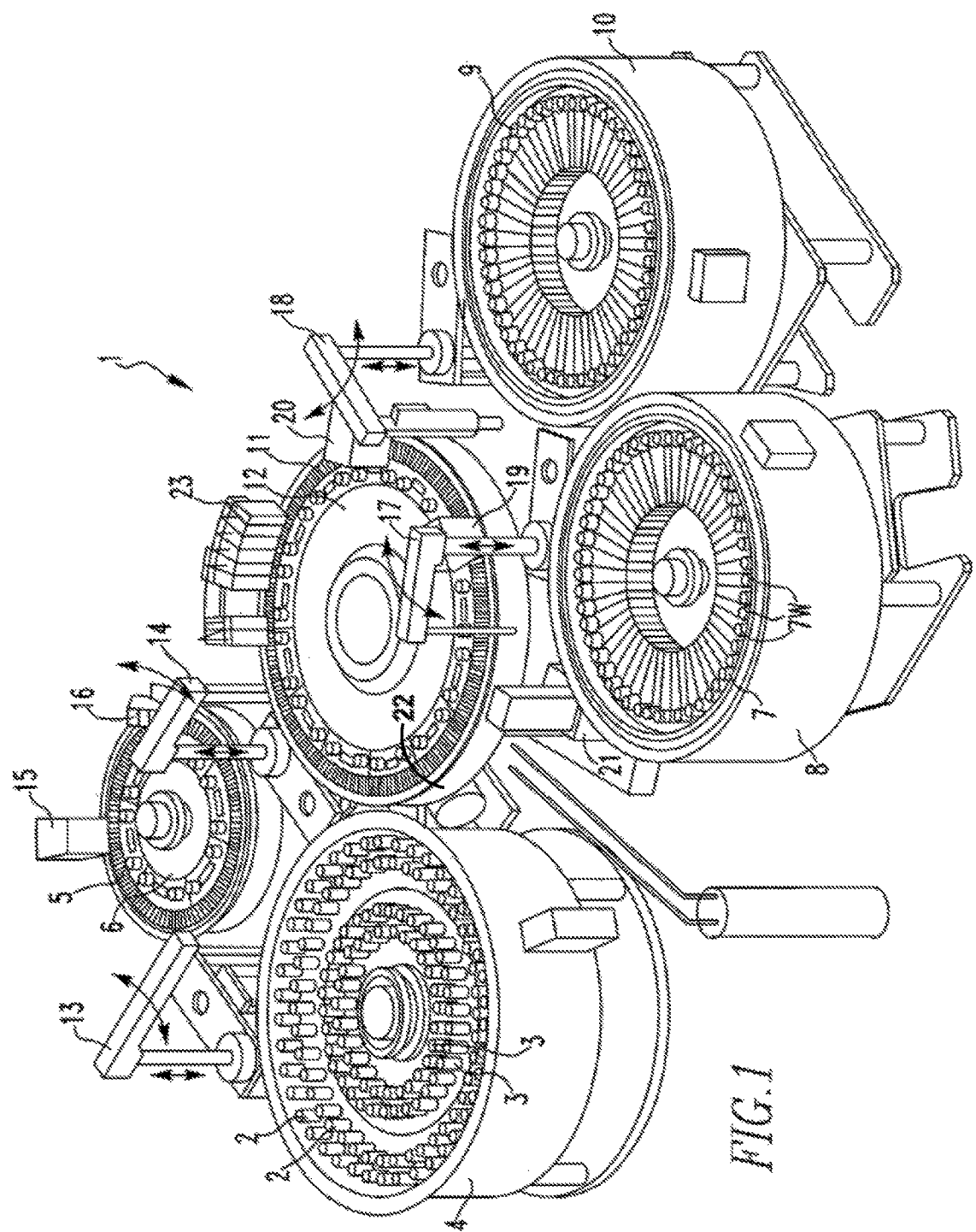
FIG. 1 is a perspective view of an automated clinical analyzer according to one embodiment of the present invention.

Referring to FIG. 1, there is shown an automated clinical analyzer according to the invention.

The automated clinical analyzer, generally indicated by reference numeral 1, is configured including a sample turntable 4, a diluted sample turntable 6, a first reagent turntable 8, a second reagent turntable 10, and a reaction turntable 12.

Two rows of sample containers 2, each row consisting of a given number of sample containers 2, are set on the sample turntable 4 near its outer periphery. Each sample container 2 holds a sample therein. Two rows of diluent cuvettes 3 are set on the sample turntable 4 inside the two rows of the sample containers 2. Each diluent cuvette 3 in one row holds a calibration sample. Each diluent cuvette 3 in the other row holds a sample used for accuracy management. As the sample turntable 4 is rotated, the sample containers 2 and diluted sample containers 3 on the turntable 4 are rotated at given speeds to given positions. Special diluting fluids, probes, and detergents for washing the diluted sample containers may be set at inner positions.

Diluted sample containers 5 for holding samples, which have been drawn in from the sample containers 2 and diluted, are set on the diluted sample turntable 6.

A given number of first reagent containers 7 holding a first reagent in cold storage are set on the first reagent turntable 8.

A given number of second reagent containers 9 holding a second reagent in cold storage are set on the second reagent turntable 10.

A given number of reaction cuvettes 11 are set on the reaction turntable 12. A diluted sample taken from one diluted sample container 5 on the diluted sample turntable 6, an aliquot of the first reagent taken from one first reagent container 7 on the first reagent turntable 8, and an aliquot of the second reagent taken from one second reagent container 9 on the second reagent turntable 10 are put in each of the reaction cuvettes 11 such that the sample and reagents react with each other.

A sample dilution pipette 13 is disposed beside the sample turntable 4. In the automated clinical analyzer of the present embodiment, all pipettes are disposed on the side of the rotating ends of rotating arms. The sample dilution pipette 13 is driven to the left and right and up and down by a sample dilution pipette left/right and up/down moving mechanism (not shown). Thus, the pipette 13 reciprocates through a wash unit (not shown) between the sample turntable 4 and the diluted sample turntable 6 by rotating to the left and right. When the pipette 13 ascends or descends and gains access to a selected one of the sample containers 2 in a given position of the sample turntable 4, a sample pump (not shown) is operated to aspirate a given amount of sample. When the pipette has an access to a selected one of the diluted sample containers 5 at a given position of the diluted sample turntable 6, the pipette delivers a given amount of diluent (usually, normal saline solution) supplied from the pipette 13 itself together with the sample. As a result, the sample is diluted by a desired factor within the diluted sample container 5. Then, the pipette 13 is cleaned by a sample diluted pipette wash unit (not shown).

Arranged around the diluted sample turntable 6 are a sampling pipette 14, a sample dilution stirrer 15, and a diluted sample container wash unit 16, in addition to the sample dilution pipette 13. The stirrer 15 is driven up and down by a stirrer vertical drive mechanism (not shown). Also, a stirrer rod (not shown) is rotated. The stirrer rod advances into the diluted sample within a selected one of the diluted sample containers 5 on the diluted sample turntable 6 and rotates, thus diluting the sample uniformly. The diluted sample container wash unit 16 delivers the diluted sample into the reaction cuvettes 11 and then cleans the sampling pipette 14 as described later. The diluted sample container wash unit 16 has a plurality of diluted sample container wash nozzles and operates to aspirate the already detected, diluted sample from inside the diluted sample container 5 by a waste pump (not shown) via these wash nozzles, to vent the sample into the waste tank, to supply a detergent into this diluted sample container 5 by a wash pump (not shown) for washing the inside of the diluted sample container 5 with the detergent, and then to discharge the detergent into the waste tank so as to dry the inside of the diluted sample container. The diluted sample inside the diluted sample container 5 is stirred by the sample dilution stirrer 15 to dilute the sample uniformly. To allow latitude in arranging the devices 13, 14, 15, and 16, the diluted sample turntable 6 is moved in steps of a length having no common factor with the total number of the diluted sample containers 5 arranged on a circumference on the diluted sample turntable 6.

The sampling pipette 14 is driven to the left and right and up and down by the sampling pipette left/right and up/down drive mechanism (not shown) to reciprocatively rotate to the left and right between the diluted sample turntable 6 and the reaction turntable 12. When the pipette 14 ascends or descends and gains access to the diluted sample container 5 at a given position of the diluted sample turntable 6, the diluted sample pump (not shown) is operated to aspirate a given amount of diluted sample. When the pipette ascends or descends and gains access to the reaction cuvette 11 at a given position of the reaction turntable 12, the aspirated diluted sample is delivered into the reaction cuvettes 11.

Arranged around the reaction turntable 12 are a first reagent pipette 17, a second reagent pipette 18, a first reaction stirrer 19, a second reaction stirrer 20, a multi-wavelength spectrophotometer 21 being a detector, a reaction bath 22, and a reaction cuvette wash unit 23 in addition to the sampling pipette 14.

The first reagent pipette 17 is driven to the left and right and up and down by a first reagent pipette left/right and up/down drive mechanism (not shown) to reciprocate between the reaction turntable 12 and the first reagent turntable 8 by rotating to the left and right. When the first reagent pipette 17 ascends or descends and gains access to the first reagent container 7 at a given position of the first reagent turntable 8, a first reagent pump (not shown) is operated to aspirate a given amount of first reagent. When the first reagent pipette 17 ascends or descends and gains access to the reaction cuvette 11 at a given position of the reaction turntable 12, the aspirated first reagent is delivered into the reaction cuvette 11.

During the operation for delivering the first reagent into the reaction cuvette 11, a given amount of condensed reagent is diluted with pure water or room-temperature water and aliquotted by a first reagent sampling means and a first reagent diluting-and-aliquotting means (described later) in the present embodiment.

The first reaction stirrer 19 is driven up and down by a stirrer up/down drive mechanism (not shown) and has a stirrer rod (not shown) with a spinning and reciprocating motion. After advancing into the diluted sample and first reagent in the given reaction cuvette 11 on the reaction turntable 12, the stirrer rod is provided with a spinning and reciprocating motion. This permits reaction of the diluted sample to be effected uniformly and quickly.

The second reagent pipette 18 is driven to the left and right and up and down by a second reagent pipette left/right and up/down drive mechanism (not shown) to reciprocate between the reaction turntable 12 and the second reagent turntable 10 by rotating to the left and right. When the second reagent pipette 18 ascends or descends and gains access to the second reagent container 9 at a given position of the second reagent turntable 10, a second reagent pump (not shown) is operated to aspirate a given amount of second reagent. When the second reagent pipette 18 ascends or descends and gains access to the reaction cuvette 11 at a given position of the reaction turntable 12, the aspirated second reagent is delivered into the reaction cuvette 11.

During the operation in which the second reagent is delivered into the reaction cuvette 11, a given amount of condensed reagent is diluted with pure water or room-temperature water and aliquotted in the present embodiment by a second reagent sampling means and a second reagent dilution-and-aliquotting means (described later) in the same way as in the case of the first reagent.

The second reaction stirrer 20 is driven up and down by a stirrer up/down drive mechanism (not shown) and has a stirrer rod (not shown) with a spinning and reciprocating motion. After advancing into the diluted sample and second reagent in the given reaction cuvette 11 on the reaction turntable 12, the stirrer rod is provided with a spinning and reciprocating motion. As a result, the diluted sample reacts uniformly and quickly.

The multi-wavelength spectrophotometer 21 measures the absorbance of the diluted sample in the reaction cuvette 11 and detects how the diluted sample reacts inside the reaction cuvette 11. The reaction bath 22 maintains constant the temperature of the reaction cuvette 11 on the reaction turntable 12 at all times.

Figure 5:
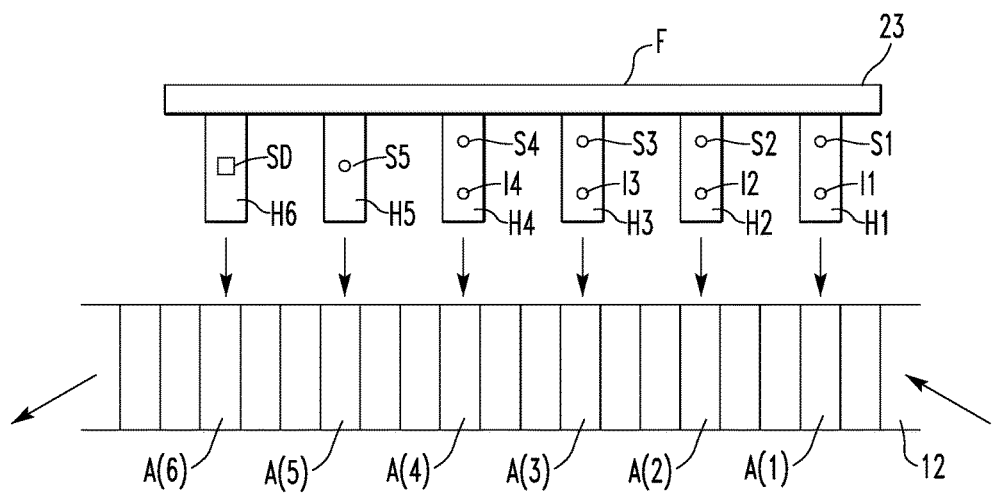
FIG. 5 is a diagram illustrating the configuration of a reaction cuvette wash unit.

As described previously, the reaction cuvette wash unit 23 has the structure shown in FIG. 5. The wash unit 23 performs analysis routine cleaning using the first detergent by means of the reaction cuvette wash nozzles S1-S5, I1-I4, and drying nozzle SD.

To allow latitude in arranging the sampling pipette 14, first reagent pipette 17, second reagent pipette 18, first reaction stirrer 19, second reaction stirrer 20, multi-wavelength spectrophotometer 21, reaction bath 22, and reaction cuvette wash unit 23, the reaction turntable 12 is moved in steps of a length having no common factor with the total number of the reaction cuvettes 11 arranged on a circumference on the reaction turntable 12.

The inventive portions of the present embodiment are next described.

Figure 2:
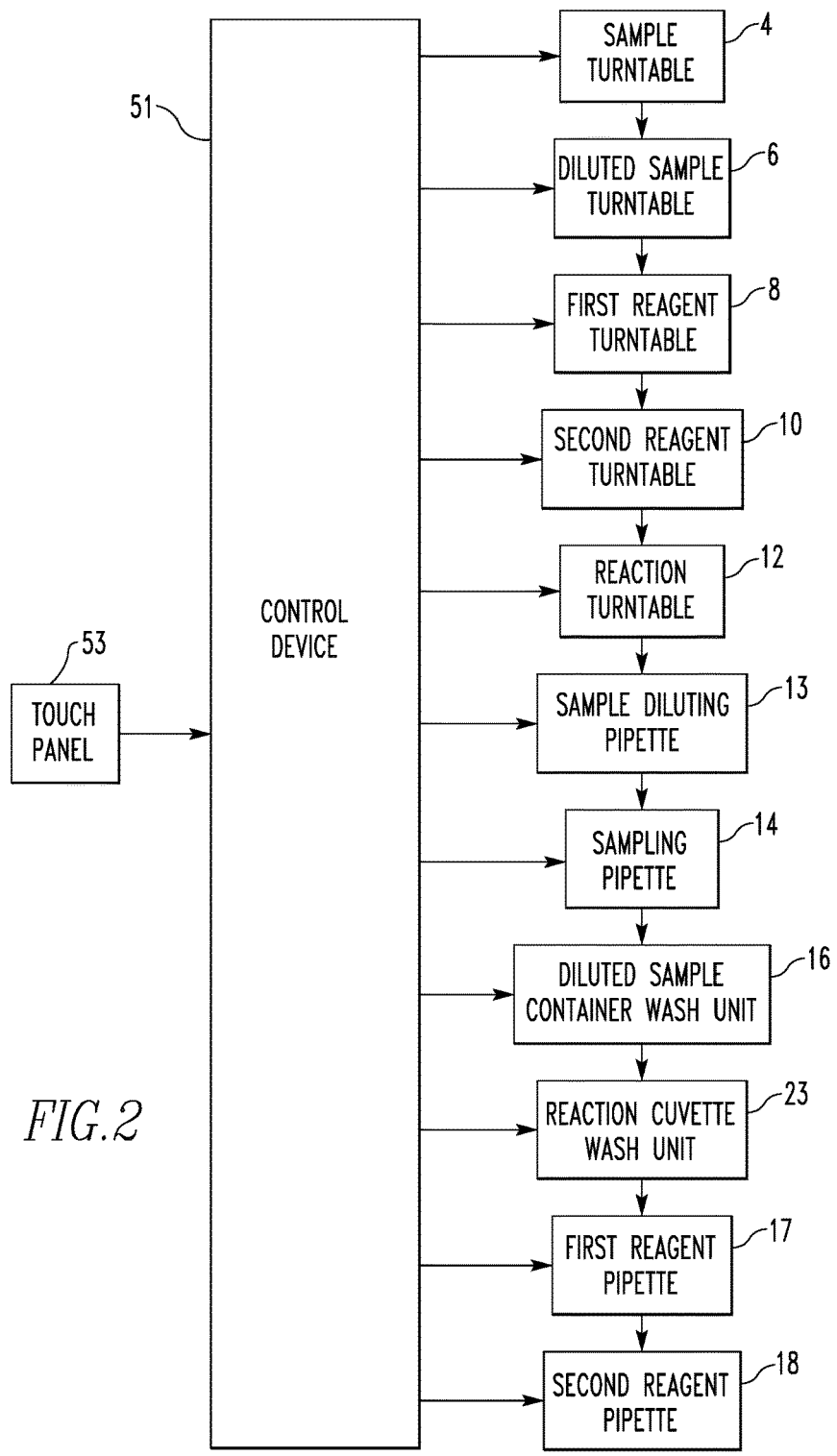
FIG. 2 is a block diagram of the inventive electrical configuration of the analyzer shown in FIG. 1.

FIG. 2 is a block diagram of the electrical components of the inventive portions. The electrical components include control device or system 51 that receives instructions from a touch panel 53 which displays the states of a first switch for starting wash of the reaction cuvette wash nozzles of the reaction cuvette wash unit 23, a second switch for starting wash of the diluted sample container wash nozzles of the diluted sample container wash unit 16, a switch for specifying the number of wash steps performed by each wash nozzle, and a switch for specifying the types of detergents used to clean the wash nozzles. The control device 51 controls the operation of the sample turntable 4, diluted sample turntable 6, first reagent turntable 8, second reagent turntable 10, reaction turntable 12, sample dilution pipette 13, sampling pipette 14, diluted sample container wash unit 16, reaction cuvette wash unit 23, first reagent pipette 17, and second reagent pipette 18.

Figure 3:
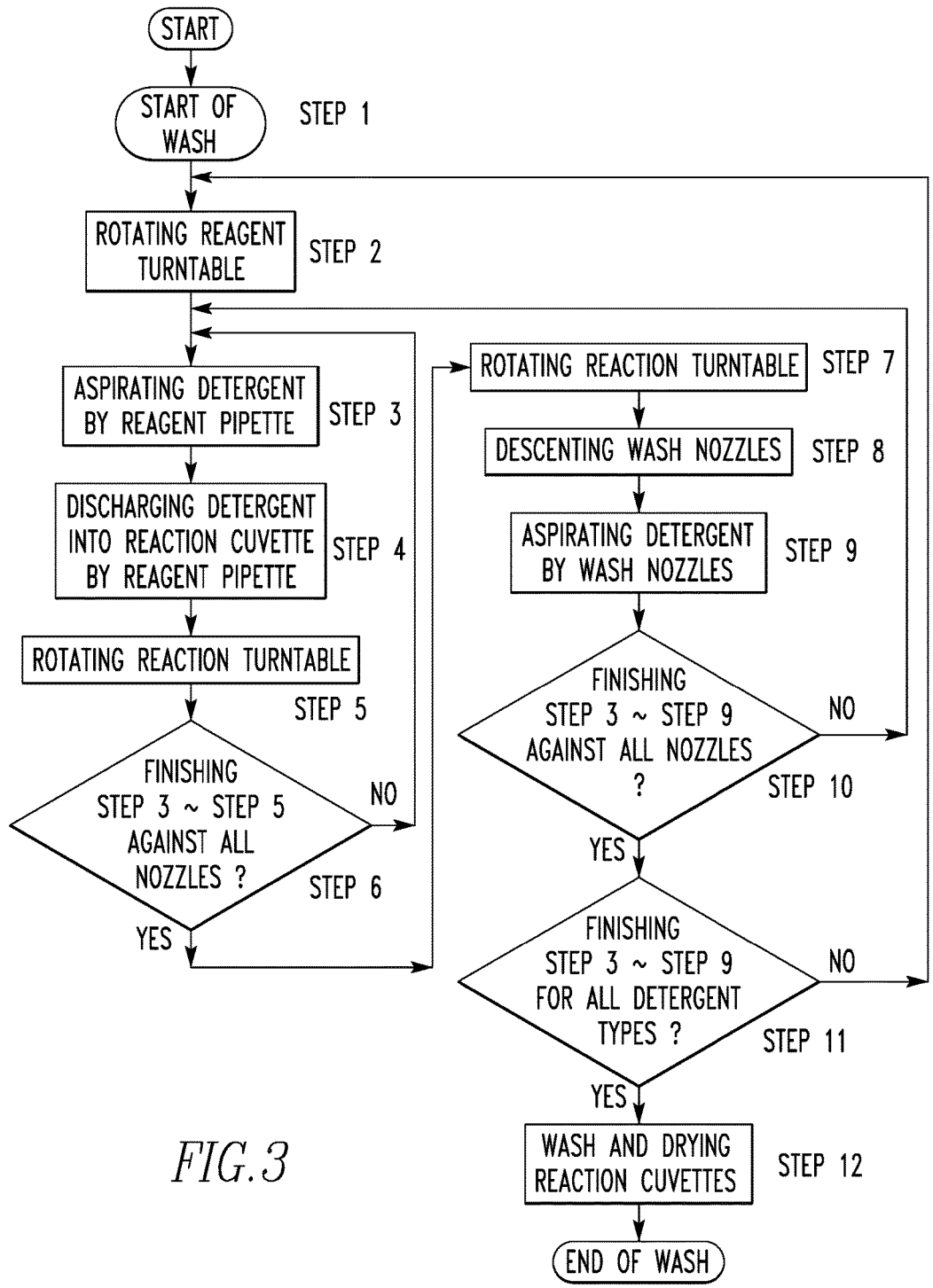
FIG. 3 is a flowchart illustrating a first wash process performed under control of the control device of the analyzer shown in FIG. 2.

The operation of the control device that cleans the reaction cuvette nozzles of the reaction cuvette wash unit is next described by referring to FIG. 3, which is a flowchart illustrating the operation of the control device.

Prior to nozzle cleaning, plural detergent containers 7W holding plural types of the second detergent (e.g., alkaline detergent, acidic detergent, and cleaning agent (such as hypochlorite detergent)) for nozzle cleaning are arranged on a reagent turntable (in the present embodiment, the first reagent turntable 8).

When the first switch of the touch panel 53 is depressed (turned on) (step 1), the control device 51 moves the first reagent turntable 8 into a position where the first reagent pipette 17 can suck any one of the detergent containers 7W containing the second detergent (step 2).

The second detergent is aspirated by the first reagent pipette 17 (step 3), and the detergents are delivered into the reaction cuvettes 11 on the reaction cuvette turntable (herein also referred to as the reaction turntable) 12 (step 4). The quantity of detergent of this time is set to quantity to reach the height of the overflow nozzles.

The reaction turntable 12 is driven to move the reaction cuvette 11 from which the second detergent is scheduled to be next delivered into a position where the first reagent pipette 17 can aspirate and deliver the detergents (step 5).

Steps 3-5 are performed as many times as the number of the nozzles of the reaction cuvette wash unit 23 which perform sucking operations (step 6). Consequently, the second detergent is injected into the five reaction cuvettes A-E corresponding to the array of the nozzles S1-S5 to be cleaned as shown in FIG. 6A.

Figure 6B:
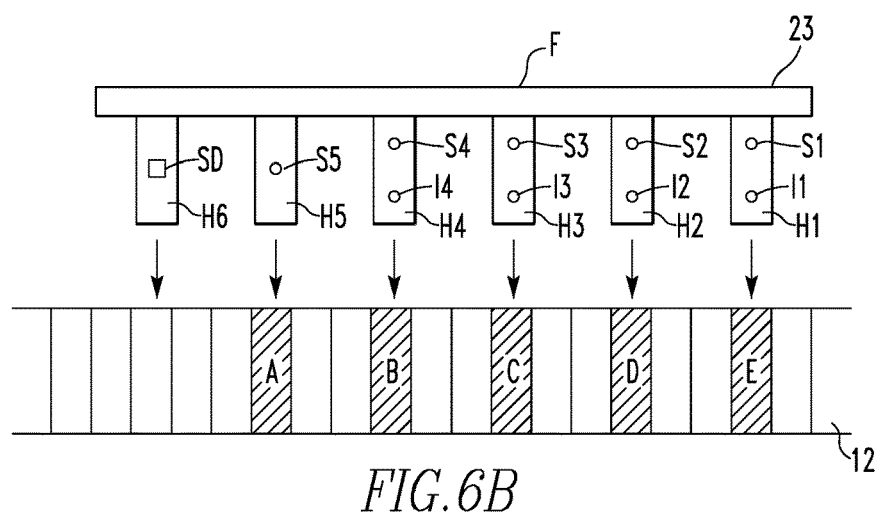
FIGS. 6A and 6B are diagrams illustrating the manner in which a second detergent is injected into a reaction cuvette.
Figure 6A:
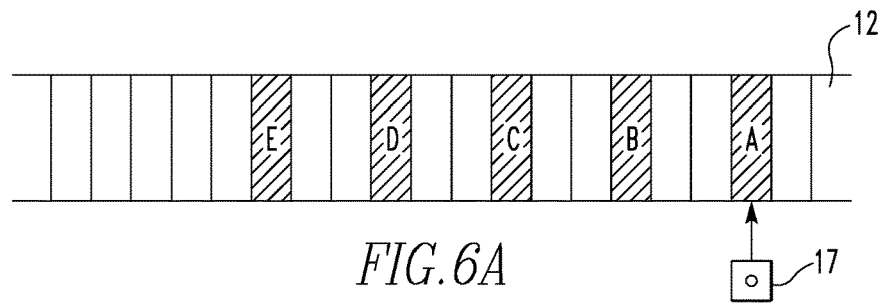

The reaction turntable 12 is driven to bring the reaction cuvettes 11 of E-A containing the detergents under the nozzles S1-S5 of the reaction cuvette wash unit 23 to be cleaned as shown in FIG. 6B (step 7). The nozzles of the wash unit 23 are made to descend (step 8). The second detergent is aspirated from inside the reaction cuvettes 11 via the nozzles S1-S5 and via the anti-overflow nozzles (step 9).

Steps 3-9 are performed as many times as a specified number of cleaning steps (step 10).

Steps 3-10 are performed as many times as a specified number of types of the second detergent while varying the type of the second detergent used (step 11).

Finally, the reaction cuvette wash unit 23 is driven to clean and dry the inside of the reaction cuvette 11 used for the nozzle cleaning (step 12). In this step, the aforementioned analysis routine cleaning may be done for all the reaction cuvettes.

Figure 4:
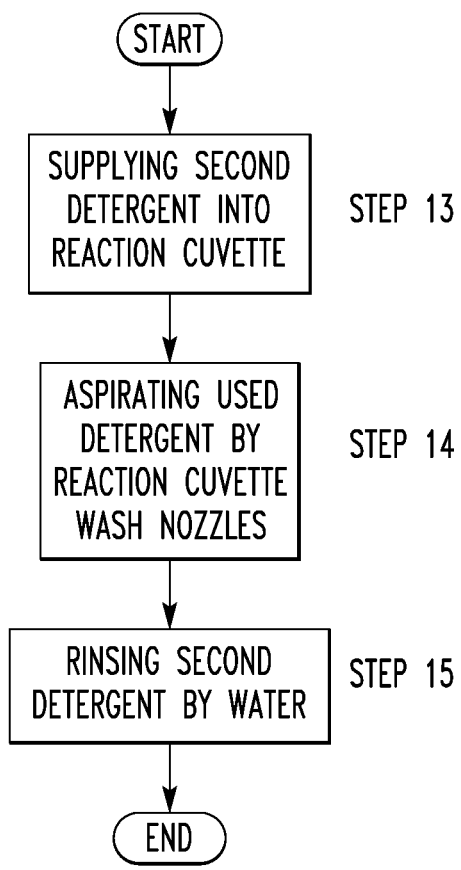
FIG. 4 is a flowchart illustrating a second wash process performed under control of the control device of the analyzer shown in FIG. 2.

The first wash process has been described so far. Referring to the flowchart of FIG. 4, after the first wash process, a separately prepared second detergent is supplied into the reaction cuvettes to clean their insides (step 13). Then, the used detergent is aspirated by the reaction cuvette wash nozzles and discharged (step 14). Furthermore, water is poured into the reaction cuvettes to wash out the residues of the second detergent in the reaction cuvettes. The water is then drawn in by the reaction cuvette wash nozzles and discharged (step 15). These three steps constitute a second rinsing process. In this second rinsing process, the above described analysis routine cleaning mode can be adopted. Usually, an alkaline detergent is preferably used in this second rinsing process.

The diluted sample container wash unit 16 for cleaning the diluted sample containers is also provided with plural wash nozzles which can be similarly cleaned. That is, plural detergent containers holding plural types of detergents (such as alkaline detergent, acidic detergent, and hypochlorite detergent) are previously held on the sample turntable 4. If the second switch for starting wash of the diluted sample container wash nozzles of the diluted sample container wash unit 16 is turned on, then the control device 51 delivers the detergents into the diluted sample containers 5 on the diluted sample turntable 6 by the use of the sample dilution pipette 13 and cleans the wash nozzles of the diluted sample container wash unit 16 with the detergents within the diluted sample container 5, in the same way as when the first switch is turned on. Then, the dilution wash unit is rinsed with an alkaline detergent, thus terminating the cleaning process.

According to this simple configuration, the reaction cuvette wash nozzles of the reaction cuvette wash unit 23 can be cleaned with simple manipulations. Furthermore, the diluted sample wash nozzles of the diluted sample container wash unit 16 can be cleaned with a simple structure and easy manipulations. It is to be noted that the present invention is not restricted to the above embodiment.

In the description of the above embodiment, all the nozzles are cleaned. Instead, specified one or more of the nozzles may be cleaned. In this case, the cleaned nozzles may be specified from the touch panel 53. Furthermore, in the above embodiment, the control device 51 uses the detergent put in the first reagent containers 7 on the first reagent turntable 8. Alternatively, the control device 51 may use the detergent put in the second reagent containers 9 on the second reagent turntable 10.

Furthermore, the operation for washing the wash nozzles of the wash unit of the present embodiment may be interlocked with normal operation of the diluted sample container wash unit 16 to clean the diluted sample containers 5 and with normal operation of the reaction cuvette wash unit 23 to clean the reaction cuvettes 11. In this case, the interlocking may be activated or deactivated using the touch panel 53.

In addition, after wash of the wash nozzles of the wash unit of the present embodiment, the power supply of the automated analyzer may be automatically turned off. In this case, the automatic power-off mode may be selectively deactivated from the touch panel 53.

Further, in the above embodiment, in order to clean the wash nozzles of the reaction cuvette wash unit at once, aliquots of detergent as many as there are nozzles are injected successively (see step 6). After executing steps 1-4, steps 7-9 may be performed. Then, the process may return to step 1. Then, steps 1-4 and steps 7-9 may be performed as many times as there are nozzles. In this modified embodiment, when the second detergent is delivered into the reaction cuvette 11 (indicated by A in FIG. 6A), the reaction turntable 12 is driven to move this reaction cuvette 11 into the position of the nozzle S5 as shown in FIG. 6B. The second detergent is sucked from this reaction cuvette by the nozzle S5. During the suction using the nozzle S5, the second detergent cooperating with the reagent pipette 17 to perform next nozzle cleaning can be injected into the reaction cuvette 11. In consequence, the nozzle can be cleaned in substantially the same time as for the above-described embodiment.

Furthermore, in the above embodiment, the containers 7W containing detergents for nozzle cleaning are held on the first reagent turntable 8. The invention is not restricted to this arrangement. The containers 7W may also be held on the second reagent turntable 10. Additionally, the containers 7W may be placed at any locations if suction using either the first reagent pipette 17 or the second reagent pipette 18 is possible.

Having thus described my invention with the detail and particularity required by the Patent Laws, what is desired protected by Letters Patent is set forth in the following claims.

The invention claimed is:

1. A cleaning method adapted to be implemented in an automated clinical analyzer having a sample turntable on which sample containers are set, a reagent turntable on which reagent containers are set, a reaction turntable on which a plurality of reaction cuvettes are set, a reagent pipette for aspirating a reagent from each of the reagent containers on the reagent turntable and delivering the aspirated reagent into the plurality of reaction cuvettes on the reaction turntable, a reaction cuvette wash unit for cleaning the plurality of reaction cuvettes set on the reaction turntable, the reaction cuvette wash unit having plural exhaust nozzles (S1-S5) for aspirating reaction liquids, a first detergent or rinse fluid from inside the plurality of reaction cuvettes, and having injection nozzles (11-14) for delivering a first detergent or rinse fluid into the plurality of reaction cuvettes, said exhaust nozzles being equally spaced apart by a distance corresponding to the width of the plurality of reaction cuvettes, delivering and aspirating a first detergent, and delivering and aspirating a rinse fluid, and a control device controlling the operation of the sample turntable, the reagent turntable, the reaction turntable, the reagent pipette, and reaction cuvette wash unit, said cleaning method in a nozzle cleaning mode comprising the steps of:

placing a second detergent container for holding a second detergent in a position where the second detergent can be aspirated by the reagent pipette;

driving the reagent pipette and reaction turntable such that the second detergent is aspirated and delivered into the plurality of reaction cuvettes whose positions are apart corresponding to the positions of the exhaust nozzles;

driving the reaction turntable to move the reaction cuvettes holding the second detergent therein into the position of the exhaust nozzles of the reaction cuvette wash unit; and making these exhaust nozzles descend simultaneously to simultaneously aspirate the second detergent from inside the plurality of reaction cuvettes, thus cleaning the exhaust nozzles, wherein after the step of making the exhaust nozzles descend simultaneously to simultaneously aspirate the second detergent from inside the reaction cuvettes, a residue of the second detergent remaining in the reaction cuvettes is removed by a separate detergent washing and rinsing process by the reaction cuvette wash unit, wherein both the first and second detergents include at least one of an alkaline detergent, an acidic detergent, and a hypochlorite detergent.

* * * * *

UNITED STATES PATENT AND TRADEMARK OFFICE
CERTIFICATE OF CORRECTION

| | |
|---|---|
| PATENT NO. | : 10,254,302 B2 |
| APPLICATION NO. | : 15/297827 |
| DATED | : April 9, 2019 |
| INVENTOR(S) | : Yoshiyuki Nakayama |

Page 1 of 1

It is certified that error appears in the above-identified patent and that said Letters Patent is hereby corrected as shown below:

In the Claims

Column 10, Line 10, Claim 1, delete "(11-14)" and insert -- (I1-I4) --

Signed and Sealed this
Sixteenth Day of July, 2019

Andrei Iancu
*Director of the United States Patent and Trademark Office*